United States Patent
Gapp et al.

(10) Patent No.: US 9,149,349 B2
(45) Date of Patent: Oct. 6, 2015

(54) SYSTEM FOR PRODUCING DENTAL MOLDINGS

(75) Inventors: Wolfgang Gapp, Bad Wurzach (DE); Pius Steinhauser, Leutkirch (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 846 days.

(21) Appl. No.: 13/408,537

(22) Filed: Feb. 29, 2012

(65) Prior Publication Data

US 2012/0233830 A1    Sep. 20, 2012

(30) Foreign Application Priority Data

Mar. 18, 2011   (DE) .......................... 10 2011 005 797

(51) Int. Cl.
  *B23B 31/107*    (2006.01)
  *A61C 13/00*     (2006.01)

(52) U.S. Cl.
  CPC ......... *A61C 13/0022* (2013.01); *B23B 31/1075* (2013.01); *B23B 2231/0244* (2013.01); *B23B 2231/48* (2013.01); *Y10T 29/51* (2015.01); *Y10T 279/17769* (2015.01); *Y10T 279/17821* (2015.01); *Y10T 279/17854* (2015.01)

(58) Field of Classification Search
  CPC ........... B23B 31/1075; B23B 31/1078; A61C 13/0022
  USPC ........ 433/49, 223; 279/28, 67, 77, 83, 85, 97, 279/76, 87; 409/232, 234
  See application file for complete search history.

(56) References Cited

U.S. PATENT DOCUMENTS

| | | | | |
|---|---|---|---|---|
| 1,783,541 A | * | 12/1930 | Hogg et al. | 279/77 |
| 3,557,419 A | * | 1/1971 | Flannery | 407/36 |
| 2005/0276672 A1 | * | 12/2005 | Prince et al. | 409/234 |
| 2007/0063456 A1 | * | 3/2007 | Troxler | 279/156 |

FOREIGN PATENT DOCUMENTS

DE    102008030050 A1    8/2009

OTHER PUBLICATIONS

Notice of Reasons for Rejection from Japanese Patent Application No. 2014-101456 mailed Feb. 24, 2015.

* cited by examiner

*Primary Examiner* — Eric A Gates
*Assistant Examiner* — Paul M Janeski
(74) *Attorney, Agent, or Firm* — Marshall, Gerstein & Borun LLP

(57) ABSTRACT

A system for producing dental moldings from blanks, having a machine tool for machining a blank, and a workpiece holder for securing the blank during machining. The machine tool has in this case a mount for the workpiece holder, and the workpiece holder has a shank region that can be inserted reversibly into the mount and in the inserted state can be secured in position in the mount. Furthermore, the system has a lever element, wherein the system is configured so that the lever element can be clamped between the mount on one side and the shank region on the other side to secure the shank region in position in the mount. With such clamping of the lever element, a particularly high clamping force can be produced, by way of which the shank region of the workpiece holder can be secured in position in the mount.

9 Claims, 4 Drawing Sheets

SYSTEM FOR PRODUCING DENTAL MOLDINGS

BACKGROUND OF THE INVENTION

1. Field of the Invention

The invention relates to a system for producing dental mouldings from blanks, which has a machine tool for machining a blank, and also a workpiece holder for securing the blank during machining, wherein the machine tool has a mount for the workpiece holder, and wherein the workpiece holder has a shank region which can be inserted reversibly into the mount and in the inserted state can be secured in position in the mount.

2. Related Technology

Such a system is known from DE 10 2008 030 050 A1. With this system, the workpiece holder can be locked in a precise and reproducible manner in the mount of the machine tool. However, with this known system, it is possible—in particular in the case of blanks having a relatively long shape—for the clamping force with which the workpiece holder is secured in position in the mount to be limited so that a particular desired degree of precision in the machining of the blank can no longer be achieved.

SUMMARY OF THE INVENTION

The invention provides a correspondingly improved system for producing dental moldings from blanks. Preferably, according to the invention it is possible for the workpiece holder to be secured in position in the mount particularly well.

Accordingly, the invention provides a system for producing dental moldings from blanks, which has a machine tool for machining a blank, and a workpiece holder for securing the blank during machining. The machine tool has in this case a mount for the workpiece holder, and the workpiece holder has a shank region that can be inserted reversibly into the mount and in the inserted state can be secured in position in the mount. Furthermore, the system has a lever element, that can be clamped between the mount on one side and the shank region on the other side in order to secure the shank region in position in the mount.

With such clamping of the lever element, a particularly high clamping force can be produced, by way of which the shank region of the workpiece holder can be secured in position in the mount.

Preferably, the system further has a threaded pin that is inserted in a rotatable manner into a threaded bore in the lever element so that it can be pressed against a pressure surface of the shank region by rotation in the threaded bore to clamp the lever element between the mount and the shank region. As a result, the lever element can be clamped between the shank region and the mount in a particularly effective manner and with comparatively simple handling.

Preferably, the lever element forms a two-sided lever, preferably an angle lever, which acts between the mount and the shank region. As a result, particularly effective lever ratios for clamping the shank region of the workpiece holder in the mount can be achieved. Preferably, in this case, the threaded bore is arranged, with regard to a pivot point of the lever element, on a first side of the two-sided lever. Further preferably, the lever element has, with regard to the pivot point of the lever element, on a second side opposite the first side, at least one abutment surface for abutment against the shank region. As a result, particularly good transmission can be achieved during clamping. Highly preferably, in this case, a first abutment surface and a second abutment surface can be formed.

Preferably, the shank region has a first planar surface region and a second planar surface region, wherein the second planar surface region is configured so that it is not parallel to the first planar surface region, and wherein furthermore the mount has a first planar surface region and a second planar surface region, so that, when the lever element is clamped, the first planar surface region of the shank region comes into surface contact with the first planar surface region of the mount and the second planar surface region of the shank element comes into surface contact with the second planar surface region of the mount. Further preferably, in this case, the shank region has a longitudinal axis, wherein the first planar surface region of the shank region and the second planar surface region of the shank region are configured so that they each extend parallel to the longitudinal axis.

BRIEF DESCRIPTION OF THE DRAWINGS

The invention is explained in more detail in the following text on the basis of an exemplary embodiment and with reference to the drawings, in which.

DETAILED DESCRIPTION

Figure 1:
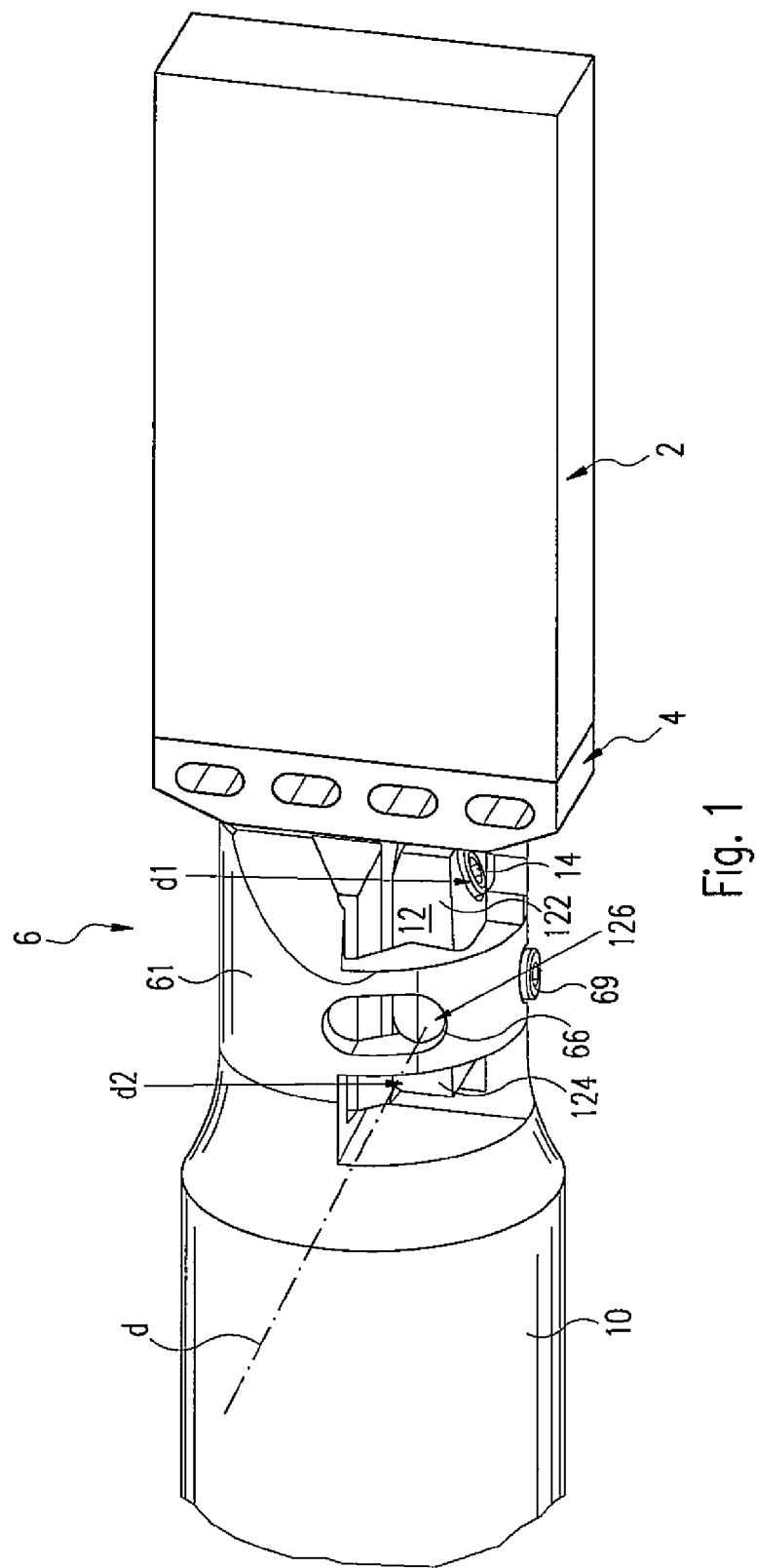
FIG. 1 shows a sketch of the system according to the exemplary embodiment in the region of the mount for the workpiece holder.
Figure 3:
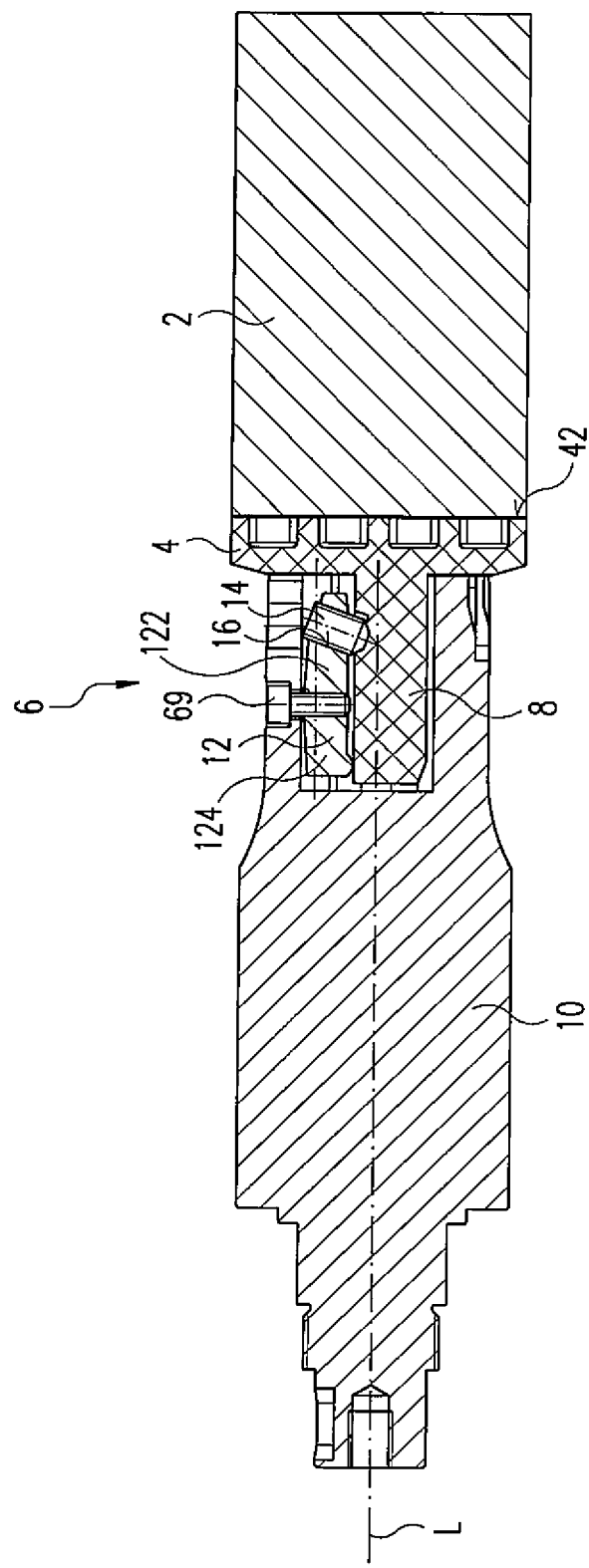
FIG. 3 shows a longitudinal section through the region around the mount.

FIG. 1 shows a sketch of a region relating to the invention of a system according to the invention for producing dental mouldings from blanks. The system comprises a machine tool (not shown in its entirety) for machining a blank 2. The machine tool has a workpiece holder 4 for securing the blank 2 during the machining process for producing a dental molding from the blank 2. FIG. 3 shows a corresponding sectional illustration. The workpiece holder 4 may in particular have a planar surface 42, which is provided for the arrangement of the blank 2.

Furthermore, the machine tool has a mount 6 for the workpiece holder 4 and the workpiece holder 4 has a shank region 8, which can be inserted reversibly into the mount 6 and in the inserted state can be secured in position—preferably likewise reversibly—in the mount 6. Accordingly, the workpiece holder 4 is preferably configured so that the shank region 8 is immovable with respect to the planar surface 42. In particular, the workpiece holder 8 can be formed in one piece.

The mount 6 can, as shown by way of example in the drawing figures, be formed on an end region of a shaft element 10, for example a clamping shaft of a machine tool.

The shank region 8 of the workpiece holder 4 can be elongate, and a longitudinal axis L, which is shown by way of example in FIG. 3, can be defined by the shape of the shank region 8. The sectional illustration in FIG. 3 represents a longitudinal section in this context. The longitudinal axis L can be oriented so as to extend at right angles to the planar surface 42.

Figure 2:
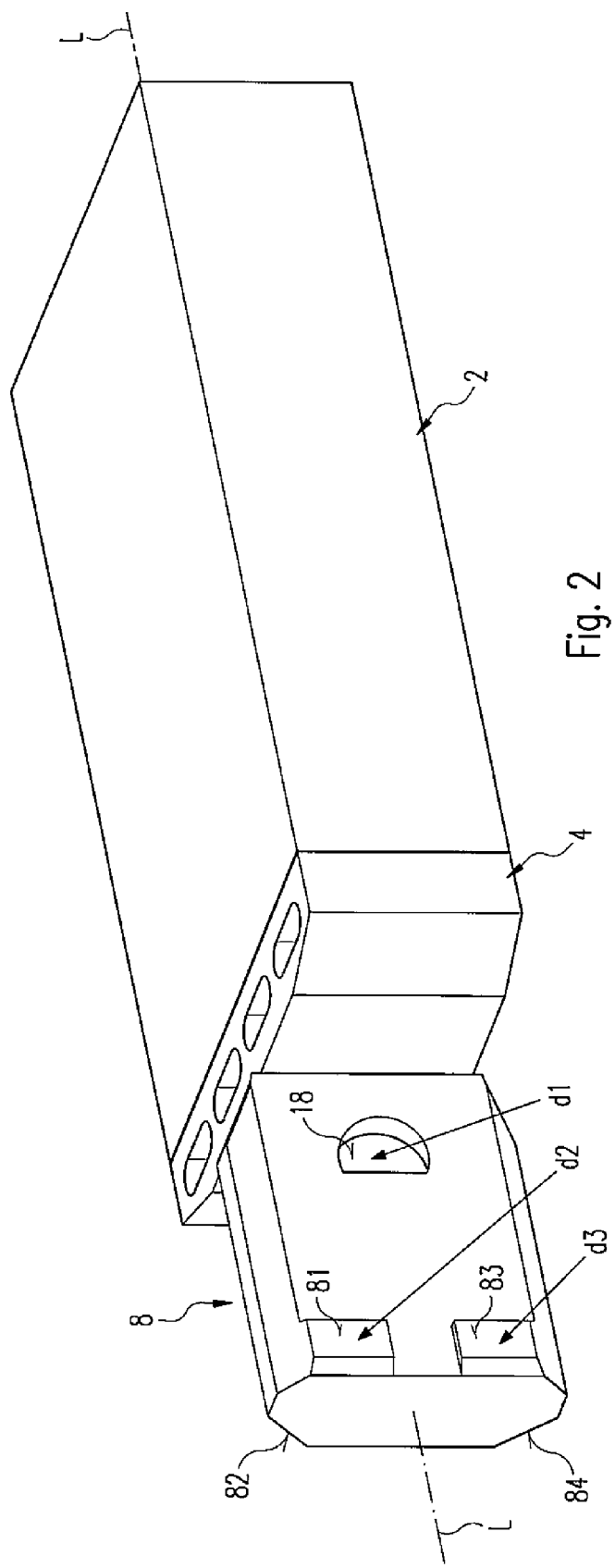
FIG. 2 shows the separated workpiece holder with the blank arranged thereon.

FIG. 2 illustrates the workpiece holder 4, with the blank 2 arranged thereon, in separated form.

The mount 6 may comprise an annular part 61, which is illustrated by way of example in FIG. 1 and which, with the shank region 8 of the workpiece holder 6 inserted and secured in position, engages around the shank region 8 so as to enclose it in an annular manner, in particular so as to enclose the longitudinal axis L in an annular manner.

Furthermore, the system has a lever element 12. The system is in this case configured so that the lever element 12 can be clamped between the mount 6 on one side and the shank region 8 on the other side in order to secure the shank region 8 in position in the mount 6. For example, the configuration may be such that, in the clamped state, the lever element 12 is supported against an abutment region of the annular part 61.

With such clamping, a particularly high clamping force for securing the shank region 8 or the workpiece holder 4 in position in the mount 6 can be achieved. In this way, it is possible, for example, for a titanium blank having an extent of about 70 mm along the longitudinal axis L to be machined with sufficient or particularly high precision.

Preferably, the system furthermore has a threaded pin 14 which is inserted in a rotatable manner into a threaded bore 16 in the lever element 12 in such a way that it can be pressed against a pressure surface 18 of the shank region 8 by rotation in the threaded bore 16 in order to clamp the lever element 12 between the mount 6 and the shank region 8. As a result, the lever element 12 can be clamped between the shank region 8 and the mount 6 in a particularly effective manner and with comparatively simple handling. The clamping force, by way of which the shank region 8 is clamped in the mount 6, can be increased particularly effectively by corresponding rotation of the threaded pin 14 in the threaded bore 16.

Preferably, the pressure surface 18 is configured in an inclined manner, that is to say not parallel to the longitudinal axis L. For example, it can be provided for the pressure surface 18 to enclose an angle of between 10° and 30° with the longitudinal axis L. The pressure surface 18 can be formed so that a surface normal of the pressure surface 18 has a component that is directed in the direction of the planar surface 42 of the workpiece holder 4.

Preferably, the lever element 12 forms a two-sided lever, highly preferably an angle lever, which acts between the mount 6 and the shank region 8. As a result, the lever element 12 can form so to speak a rocker, which acts as an angle lever between the mount 6 and the shank region 8. A corresponding pivot point 126 and an axis of rotation d of the lever element 12 acting as a rocker are indicated in FIG. 1. The axis of rotation d is in this case preferably—when the workpiece holder 4 is inserted as provided in the mount 6—formed so as to be oriented in a manner extending at right angles to the longitudinal axis L of the shank region 8. The configuration is furthermore such that the axis of rotation d passes through the annular part 61. The mount 6 can in particular have a rest 66 for supporting the lever element 12 in order to form the axis of rotation d. The rest 66 is preferably formed on the annular part 61.

Particularly effective lever ratios for clamping the workpiece holder 4 in the mount 6 can be achieved with such a configuration of the lever element 12.

Preferably, in this case, the threaded bore 16 is arranged, with regard to the pivot point 126 or the axis of rotation d of the lever element 12, on a first side 122 of the two-sided lever. As a result, the clamping force can be transmitted preferably by the pivot point 126 or the axis of rotation d starting from the threaded pin 14. At the same time, the effective lever arm for supporting the workpiece holder 4 is increased in size, for example tripled, compared with single support.

Further preferably, at least one abutment surface for abutment against the shank region 4 is formed on the corresponding second side 124 of the two-sided lever. As a result, particularly good lever ratios for clamping can be achieved. For example, two such abutment surfaces can be provided on the lever element 12, these abutment surfaces being spaced apart from one another, in particular as seen along the axis of rotation d.

The shank region 8 can have receiving surfaces 81, 83 corresponding hereto. In this way, the lever element 12 can be braced against the shank region 8 via three points d1, d2, d3, with a first point d1 being formed by the point of contact of the threaded pin 14 on the pressure surface 18 and the two further points d2, d3 being formed by the two direct points of contact between the abutment surfaces on the second side of the lever formed by the lever element 12, on one side, and by the corresponding receiving surfaces 81, 83 of the shank region 8, on the other side. As a result, advantageous three-point bracing can be achieved.

Figure 4:
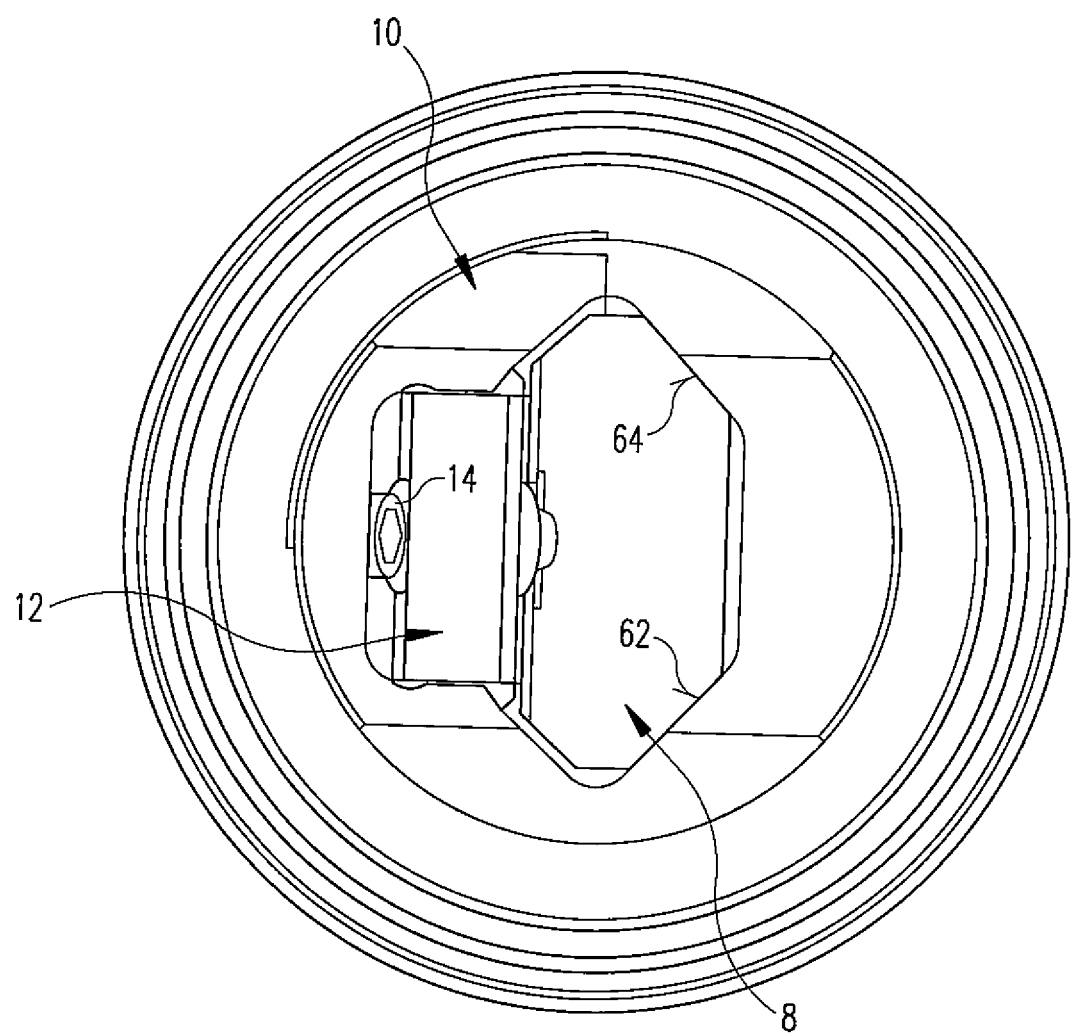
FIG. 4 shows a cross section at the level of the shank region of the workpiece holder.

As shown by way of example in FIG. 4, the shank region 8 preferably has a first planar surface region 82 and a second planar surface region 84, wherein the second planar surface region 84 is configured so that it is not parallel to the first planar surface region 82, and wherein furthermore the mount 6 has a first planar surface region 62 and a second planar surface region 64, so that, when the lever element 12 is clamped, the first planar surface region 82 of the shank region 8 comes into surface contact with the first planar surface region 62 of the mount 6 and the second planar surface region 84 of the shank element 8 comes into surface contact with the second planar surface region 64 of the mount 6. On account of the two planar surface regions 82, 84 of the shank region 8, a double wedge shape, so to speak, can be formed, and on account of the two planar surface regions 62, 64 of the mount, a correspondingly congruent abutment can be formed, so that, when the lever element 12 is clamped, the shank region 8 is pressed against the abutment and is centred thereby, and is oriented precisely.

Further advantageously, for this purpose, the first planar surface region 82 of the shank region 8 and the second planar surface region 84 of the shank region 8 are configured so that they each extend parallel to the longitudinal axis L.

The first planar surface region 62 and the second planar surface region 64 of the mount 6 can advantageously be formed at least partially on the annular part 61.

The first planar surface region 82 and the second planar surface region 84 of the shank region 8 are advantageously formed, with regard to the longitudinal axis L of the shank region 8, on a side opposite the pressure surface 18 and the receiving surfaces 81, 83. In this way, during clamping, the shank region 8 is pressed by way of its two planar surface regions 82, 84 against the two correspondingly congruent planar surface regions 62, 64 of the mount 6, and as a result an advantageously effective, defined orientation of the shank region 8 and thus of the workpiece holder 4 in the mount 6 is achieved. In other words, the double wedge shape of the workpiece holder 4 is braced by the lever element 12, acting as a rocker, against the congruent "double wedge" in the shaft element or in the mount 6.

The lever element 12 can be arranged on the mount 6, in particular on the annular part 61, in a captive manner, for example by means of a screw 69.

The invention claimed is:

1. A system for producing dental moldings from blanks, the system comprising:
   a machine tool for machining a blank;

a workpiece holder for securing the blank during machining, wherein the machine tool has a mount for the workpiece holder and the workpiece holder has a shank configured to be inserted reversibly into the mount and in the inserted state configured to be secured in position in the mount;

a lever element having a threaded bore, wherein the system is configured so that the lever element can be clamped between the mount on one side and the shank on the other side to secure the shank in position in the mount; and a threaded pin rotatably insertable into the threaded bore of the lever element, wherein rotation of the threaded pin into the threaded bore presses the lever element against the shank, thereby clamping the lever element between the mount and the shank, wherein contact between the pressed lever element and the shank is at three pressure points, each pressure point formed by at least one protrusion of the lever element or the shank.

2. The system according to claim 1, wherein the lever element forms a two-sided lever, which acts between the mount and the shank.

3. The system according to claim 2, wherein the two-sided lever is an angle lever.

4. The system according to claim 2, wherein the threaded bore is arranged, with respect to a pivot point of the lever element, on a first side of the two-sided lever.

5. The system according to claim 4, wherein the lever element has, with respect to the pivot point of the lever element, on a second side opposite the first side, at least one abutment surface for abutment against the shank.

6. The system according to claim 5, wherein the lever element has, on the second side, a first abutment surface and a second abutment surface for abutment against the shank region.

7. The system according to claim 1, wherein:
the shank has a first planar surface region and a second planar surface region configured so that it is not parallel to the first planar surface region, and
the mount has a first planar surface region and a second planar surface region, so that, when the lever element is clamped, the first planar surface region of the shank comes into surface contact with the first planar surface region of the mount and the second planar surface region of the shank comes into surface contact with the second planar surface region of the mount.

8. The system according to claim 7, wherein the shank has a longitudinal axis and the first planar surface region of the shank and the second planar surface region of the shank are configured so that they each extend parallel to the longitudinal axis.

9. The system according to claim 1, wherein the shank has a longitudinal axis and the pressure surface extends along an axis that is not parallel to the longitudinal axis.

* * * * *